(12) United States Patent
Huang

(10) Patent No.: US 11,045,180 B2
(45) Date of Patent: Jun. 29, 2021

(54) EXPANDING BLADE, UNIDIRECTIONAL EXPANDING DEVICE AND BIDIRECTIONAL EXPANDING DEVICE

(71) Applicant: SHANGHAI REACH MEDICAL INSTRUMENT CO., LTD., Shanghai (CN)

(72) Inventor: Xiaomin Huang, Shanghai (CN)

(73) Assignee: SHANGHAI REACH MEDICAL INSTRUMENT CO., LTD., Shanghai (CN)

( * ) Notice: Subject to any disclaimer, the term of this patent is extended or adjusted under 35 U.S.C. 154(b) by 9 days.

(21) Appl. No.: 16/627,759

(22) PCT Filed: Jan. 29, 2019

(86) PCT No.: PCT/CN2019/073656
§ 371 (c)(1),
(2) Date: Dec. 31, 2019

(87) PCT Pub. No.: WO2020/048087
PCT Pub. Date: Mar. 12, 2020

(65) Prior Publication Data
US 2020/0367874 A1 Nov. 26, 2020

(30) Foreign Application Priority Data
Sep. 7, 2018 (CN) .......................... 201811044594.0

(51) Int. Cl.
*A61B 17/02* (2006.01)
*A61B 17/00* (2006.01)

(52) U.S. Cl.
CPC ...................... *A61B 17/0206* (2013.01); *A61B 2017/00473* (2013.01)

(58) Field of Classification Search
CPC ................. A61B 17/0206; A61B 2017/00473
See application file for complete search history.

(56) References Cited

U.S. PATENT DOCUMENTS 5,993,385 A 11/1999 Johnston et al.
9,386,971 B1 * 7/2016 Casey .................. A61B 17/863
(Continued)

FOREIGN PATENT DOCUMENTS

CN 1717202 A 1/2006
CN 102497828 A 6/2012
(Continued)

OTHER PUBLICATIONS

International Search Report in PCT/CN2019/073656, issued by ISA, dated Apr. 24, 2019.
(Continued)

*Primary Examiner* — Andrew Yang
(74) *Attorney, Agent, or Firm* — Zhu Lehnhoff LLP

(57) ABSTRACT

The invention provides an expanding blade, comprising a first snap-fit portion, a second snap-fit portion, a fixation portion, a partition panel and hook edges, wherein, the first snap-fit portion has an axial flat section on one side; the second snap-fit portion is connected with the first snap-fit portion at one end and fixed to the fixation portion at the other end, and a convex locating block is arranged on the side wall of the second snap-fit portion; the partition panel is connected with the fixation portion at one end, the hook edges which are inclined outwards is arranged at the other end, and both the fixation portion and the hook edges are arranged on the same side of the partition panel. In addition, the invention also puts forward a unidirectional expanding device and a bidirectional expanding device which use the expanding blade. In this application, two fastening structures, i.e. the first snap-fit portion and the second snap-fit portion, arranged for the expanding blade can be snap-fitted in with different devices using different installation methods. Both the unidirectional expanding device and the bidirectional expanding device can also use the same kind of (Continued)

expanding blades, which reduces the number of instruments used in operations and lowers the cost, and both of them are simply fastened with simple structures, which is convenient for disassembly, assembly and replacement.

11 Claims, 6 Drawing Sheets

(56) References Cited

U.S. PATENT DOCUMENTS

| | | | |
|---|---|---|---|
| 9,848,862 B2 * | 12/2017 | Bass | ............... A61B 17/02 |
| 2009/0227845 A1 | 9/2009 | Lo et al. | |
| 2011/0257487 A1 | 10/2011 | Thalgott et al. | |

FOREIGN PATENT DOCUMENTS

| | | | |
|---|---|---|---|
| CN | 104473665 A | 4/2015 |
| CN | 106361390 A | 2/2017 |

OTHER PUBLICATIONS

Written Opinion of the International Search Report in PCT/CN2019/073656, issued by ISA, dated Apr. 24, 2019.

\* cited by examiner

EXPANDING BLADE, UNIDIRECTIONAL EXPANDING DEVICE AND BIDIRECTIONAL EXPANDING DEVICE

TECHNICAL FIELD

The invention relates to the field of medical devices, in particular to an expanding blade, a unidirectional expanding device and a bidirectional expanding device.

BACKGROUND

At the beginning of a spinal surgery, a small incision is cut in the skin, and the skin is pulled apart with a device to expose the spine. The expanding device which pulls the skin apart is generally bidirectionally stretched so that the small incision in the skin needs to be stretched to a large enough size with the hands or another small expanding device before it is applicable to the bidirectional expanding device. If pulled apart manually, the skin is easily damaged due to uneven tensile strength or direction deviation. If another small expanding device is used, replacement and use are inconvenient, with the blades fixedly connected with the device, making it difficult to replace.

SUMMARY OF THE INVENTION

The invention aims to provide an expanding blade, a unidirectional expanding device and a bidirectional expanding device. The expanding blade is simple in structure and convenient in disassembly and assembly. It can be not only applied to the unidirectional expanding device, but also installed to the bidirectional expanding device, making it easy to replace the expanding blade on the unidirectional expanding device or the bidirectional expanding device.

In order to achieve the above purpose, the invention puts forward an expanding blade. An expanding blade, comprising a first snap-fit portion, a second snap-fit portion, a fixation portion, a partition panel and hook edges, wherein:

The first snap-fit portion is columnar, and the first snap-fit portion has an axial flat section on one side;

The second snap-fit portion is columnar, the second snap-fit portion is connected with the first snap-fit portion at one end and fixed to the fixation portion at the other end, and a convex locating block is arranged on the side wall of the second snap-fit portion;

The partition panel is connected with the fixation portion at one end, the hook edges which are inclined outwards is arranged at the other end, and both the fixation portion and the hook edges are arranged on the same side of the partition panel.

Further, in the expanding blade, an oblique section which is inclined to the flat section is arranged for the top side surface of the first snap-fit portion.

Further, in the expanding blade, a convex ring is arranged between the first snap-fit portion and the second snap-fit portion, and the diameters of both the first snap-fit portion and the second snap-fit portion are less than the diameter of the convex ring; a boss is arranged where the second snap-fit portion and the fixation portion are connected, and the diameter of the boss is greater than that of the second snap-fit portion.

Further, in the expanding blade, the partition panel is arched, and the direction of arching is opposite to the axis of the second snap-fit portion.

Further, in the expanding blade, the hook edges are two triangular hook plates arranged at the corners of the partition panel, and an arc-like transition edge is arranged between the two hook plates.

The invention puts forward a unidirectional expanding device, which uses the expanding blade, the expanding blade is buckled with a stretching grip comprising a snap ring, a connecting rod and a gripping arm which are axially connected in a proper sequence, the stretching grip is installed to the first snap-fit portion through the snap ring, the inside diameter of the snap ring is matched with the outside diameter of the first snap-fit portion, a butt block is arranged on the inner side wall of the snap ring, and the butt block abuts on the flat section.

The invention puts forwards a bidirectional expanding device which uses the expanding blade, comprising a movable device, a fixed expanding arm, a movable expanding arm and two expanding blades, wherein:

The movable device comprises a fixation base, a movable rack and a tooth rotating knob, wherein, the fixation base has a through cavity, the movable rack is arranged in the cavity, the tooth rotating knob is rotatably fixed to the fixation base, and the tooth rotating knob is engaged with a toothed edge of the movable rack;

The fixed expanding arm has an open groove at one end, and is connected with the fixation base at the other end;

The movable expanding arm has the other clamping groove at one end, and is connected with the movable rack at the other end;

The fixed expanding arm and the movable expanding arm are arranged in parallel, the positions of the clamping grooves arranged respectively on the fixed expanding arm and the movable expanding arm correspond to each other, the hook edges of the two expanding blades are in opposite bending directions, and the clamping groove clamps the second snap-fit portion of the expanding blade;

The tooth rotating knob rotates, and the movable rack moves forward and backward in the cavity under the thrust force of the engaged toothed edges to adjust the horizontal distance between the fixed expanding arm and the movable expanding arm so that the two expanding blades respectively fastened to the fixed expanding arm and the movable expanding arm are close to or far away from each other.

Further, in the bidirectional expanding device, the clamping grooves arranged respectively on the fixed expanding arm and the movable expanding arm are in opposite open end directions.

Further, in the bidirectional expanding device, the clamping grooves are U-shaped, with arc-like groove bottoms and flush edges;

A locating hole snap-fitted in with the locating block is arranged in the center position of the groove bottom;

A concave movable cavity is arranged on the wall surface of the groove edge, a limiting clamping part is arranged in the movable cavity, the limiting clamping part is in the shape of a plate, the plate surface is flush with the wall surface of the groove edge, the limiting clamping part is arranged on the side wall of the opening of the movable cavity at one end and has a convex butt edge at the other end, and the butt edge oscillates inside and outside the movable cavity under the action of external forces.

Further, in the bidirectional expanding device, the movable device also comprises a buckle, wherein, the buckle has a bent buckling portion at one end and a pressing portion at the other end, first convex connecting portions are arranged in the middle of the buckle, second convex connecting portions are arranged on the fixation base, and the first connecting portions are rotatably connected with the second connecting portions; when the buckling portion is pressed down to the bottom end, the buckling portion is clamped between adjacent toothed edges of the movable rack, and the movable rack stops moving in the cavity; when the pressing portion is pressed, the buckling portion moves upward due to the lever principle, the buckling portion clamped between the adjacent toothed edges of the movable rack moves out, and the movable rack moves in the cavity under the adjustment of the tooth rotating knob.

Compared with the prior art, the invention has the advantage that: two fastening structures, i.e. the first snap-fit portion and the second snap-fit portion, arranged for the expanding blade can be snap-fitted in with different devices using different installation methods. In addition, both the unidirectional expanding device and the bidirectional expanding device use the same kind of expanding blades, which reduces the number of instruments used in operations and lowers the cost, and both of them are simply fastened with simple structures, which is convenient for disassembly, assembly and replacement.

Figure 1:
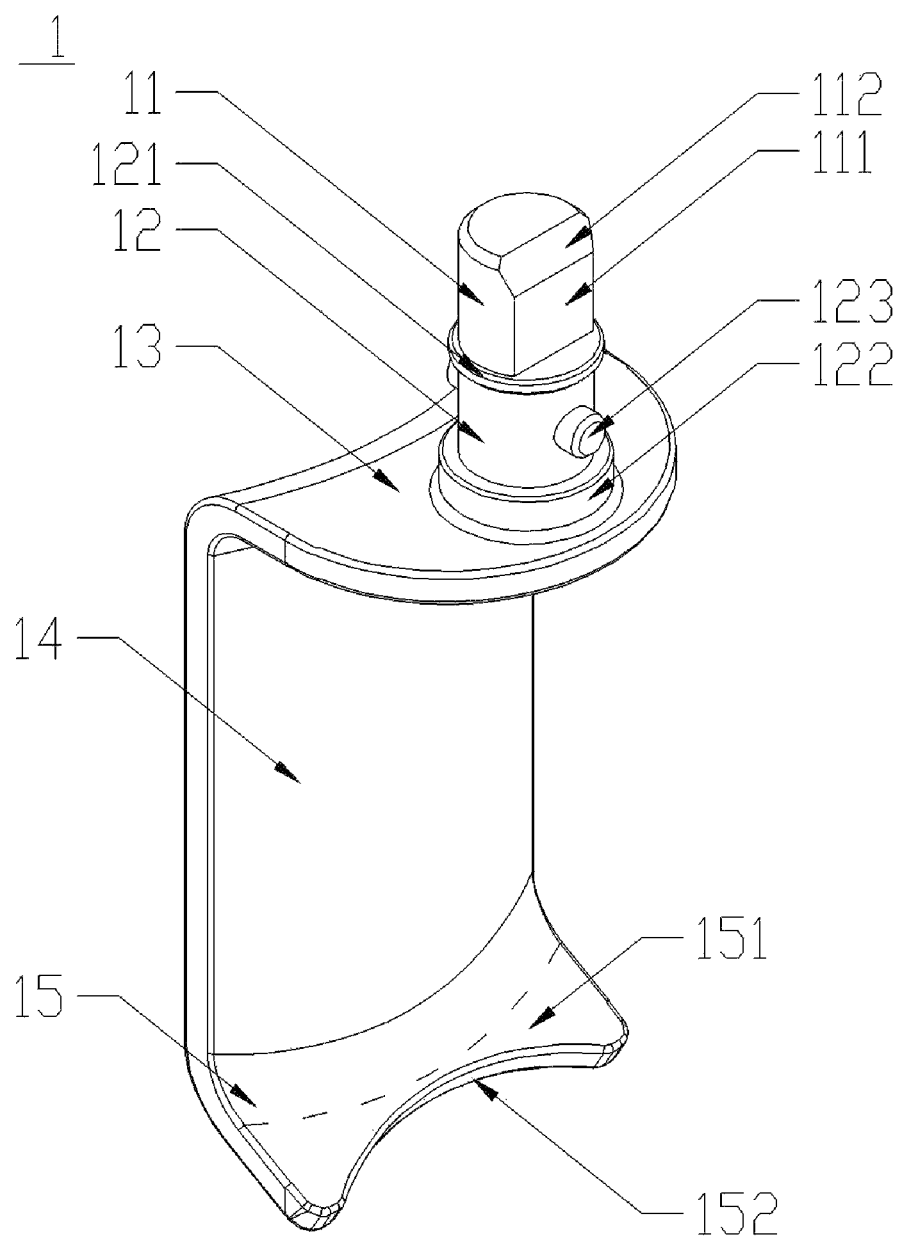
FIG. 1 is a three-dimensional structure diagram of the expanding blade in the invention.

Wherein: expanding blade 1, first snap-fit portion 11, flat section 111, oblique section 112, second snap-fit portion 12, convex ring 121, boss 122, locating block 123, fixation portion 13, partition panel 14, hook edges 15, hook plate 151, transition edge 152, stretching grip 2, snap ring 21, butt block 22, connecting rod 23, gripping arm 24, groove hole 25, fixation base 31, cavity 311, rotation position cavity 312, second connecting portions 313, buckle hole 314, movable rack 32, tooth rotating knob 33, buckle 34, buckling portion 341, first connecting portions 342, pressing portion 343, fixed expanding arm 41, movable expanding arm 42, clamping groove 5, locating hole 51, movable cavity 52, limiting clamping part 53, butt edge 54.

DETAILED DESCRIPTION OF THE PREFERRED EMBODIMENTS

A detailed description of the expanding blade of the invention is given below in combination with the schematic diagram, showing the preferred embodiment of the invention. It should be appreciated that those skilled in the art can modify the invention described herein while still achieving the advantageous effects of the invention. Therefore, it should be appreciated that the following description is widely known by those skilled in the art and not intended to limit the invention.

In the description of the invention, it should be noted that for directional words, if there are the terms "center", "transverse", "longitudinal", "length", "width", "thickness", "up", "down", "front", "back", "left", "right", "vertical", "horizontal", "top", "bottom", "inside", "outside", "clockwise", "counterclockwise" and the like which indicate the directional and positional relations as the directional or positional relations based on those shown in the figures, they are only for the convenience of describing the invention and simplifying the description, rather than indicating or implying that the device or element referred to must have a specific direction, be constructed and operated in a specific direction, and it cannot be understood as limiting the specific protection scope of the invention.

In addition, if there are terms like "first" and "second", they are used for descriptive purposes only, rather than understood as indicating or implying the relative importance or implicitly specifying the number of technical characteristics. Thus, the defined "first" and "second" characteristics may explicitly or implicitly comprise one or more such characteristics, and "at least" in the description of the invention means one or more, unless otherwise specifically defined.

In the invention, unless otherwise specified and defined, the terms "assembly", "connected" and "connection" shall be understood in a broad sense, for example, it may be fixed connection, detachable connection or integral connection; it may also be mechanical connection; it may be either direct connection or connection through an intermediate medium, and it may be the internal communication between two elements. For those of ordinary skill in the art, the specific meanings of the above terms in the invention can be understood in the light of specific conditions.

In the invention, unless otherwise specified and defined, the cases in which the first characteristic is "above" or "below" the second characteristic may include direct contact between the first characteristic and the second characteristic or contact between the first characteristic and the second characteristic through additional characteristics rather than direct contact. Moreover, the cases that the first characteristic is "above", "below" and "on" the second characteristic include that the first characteristic is directly above and obliquely above the second characteristic, or merely indicate that the level of the first characteristic is higher than that of the second characteristic. The cases that the first characteristic is "above", "below" and "under" the second characteristic include that the first characteristic is directly below or obliquely below the second characteristic, or merely indicate that the level of the first characteristic is lower than that of the second characteristic.

In the following paragraphs, the invention is described more specifically with reference to the drawings by way of example. The advantages and characteristics of the invention will be clearer according to the following description. Note that all the drawings are in very simplified forms and imprecise scales for the purpose of assisting in explaining the embodiments of the invention conveniently and clearly only.

Figure 2:
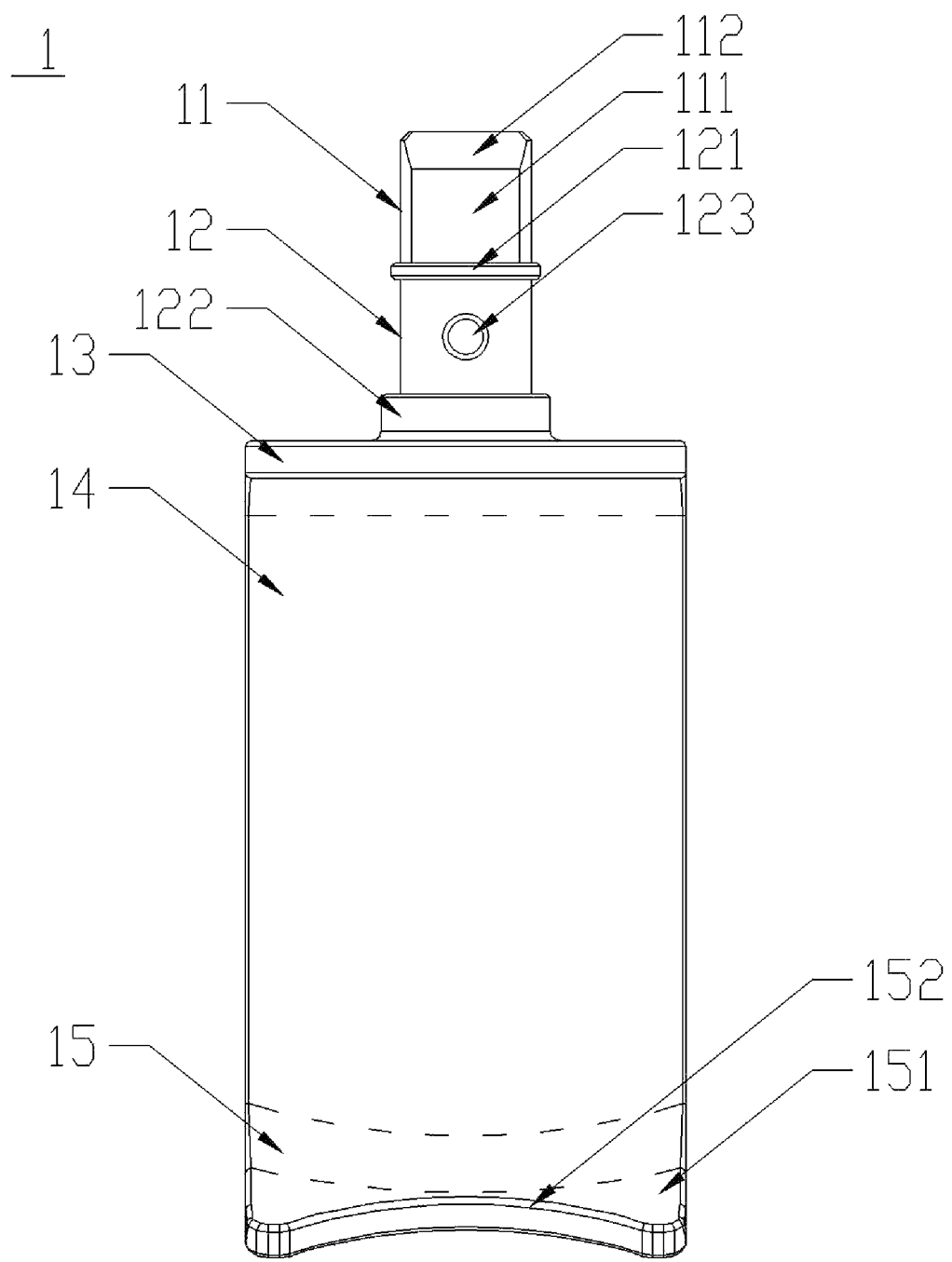
FIG. 2 is a main structure diagram of the expanding blade in the invention.

As shown in FIGS. 1 to 2, the invention puts forward an expanding blade 1. An expanding blade 1 comprises a first snap-fit portion 11, a second snap-fit portion 12, a fixation portion 13, a partition panel 14 and hook edges 15.

Specifically, as shown in FIGS. 1 to 2, the first snap-fit portion 11 is columnar, the first snap-fit portion 11 has an axial flat section 111 on one side, and an oblique section 112 which is inclined to the flat section 111 is arranged for the top side surface of the first snap-fit portion 11; the second snap-fit portion 12 is columnar, the second snap-fit portion 12 is connected with the first snap-fit portion 11 at one end and fixed to the fixation portion 13 at the other end, a convex ring is arranged between the first snap-fit portion 11 and the second snap-fit portion 12, the diameters of both the first snap-fit portion 11 and the second snap-fit portion 12 are less than the diameter of the convex ring 121, a boss 122 is arranged where the second snap-fit portion 12 and the fixation portion 13 are connected, the diameter of the boss 122 is greater than that of the second snap-fit portion 12, namely that the first snap-fit portion 11 is limited at the bottom side by the convex ring 121, and the second snap-fit portion 12 is limited by combination of the convex ring 121 and the boss 122. A convex locating block 123 is arranged on the side wall of the second snap-fit portion 12 to facilitate the locating and fastening of the second snap-fit portion 12 and to avoid misalignment of the installation angle.

In addition, as shown in FIG. 1 to FIG. 2, the partition panel 14 is connected with the fixation portion 13 at one end, and has the hook edges 15 which are inclined outwards at the other end, both the fixation portion 13 and the hook edges 15 are arranged on the same side of the partition panel 14, and the hook edges 15 are designed to facilitate the hooking and clamping of the skin and avoid skin slip. The partition panel 14 is arched, and the direction of arching is opposite to the axis of the second snap-fit portion 12. The arc-shaped partition panel 14 can better fit with the skin surface to avoid the contact between the sharp edge of the flat panel and the skin and skin damage. The hook edges 15 are two triangular hook plates 151 arranged at the corners of the partition panel 14, and an arc-like transition edge 152 is arranged between the two hook plates 151.

Figure 3:
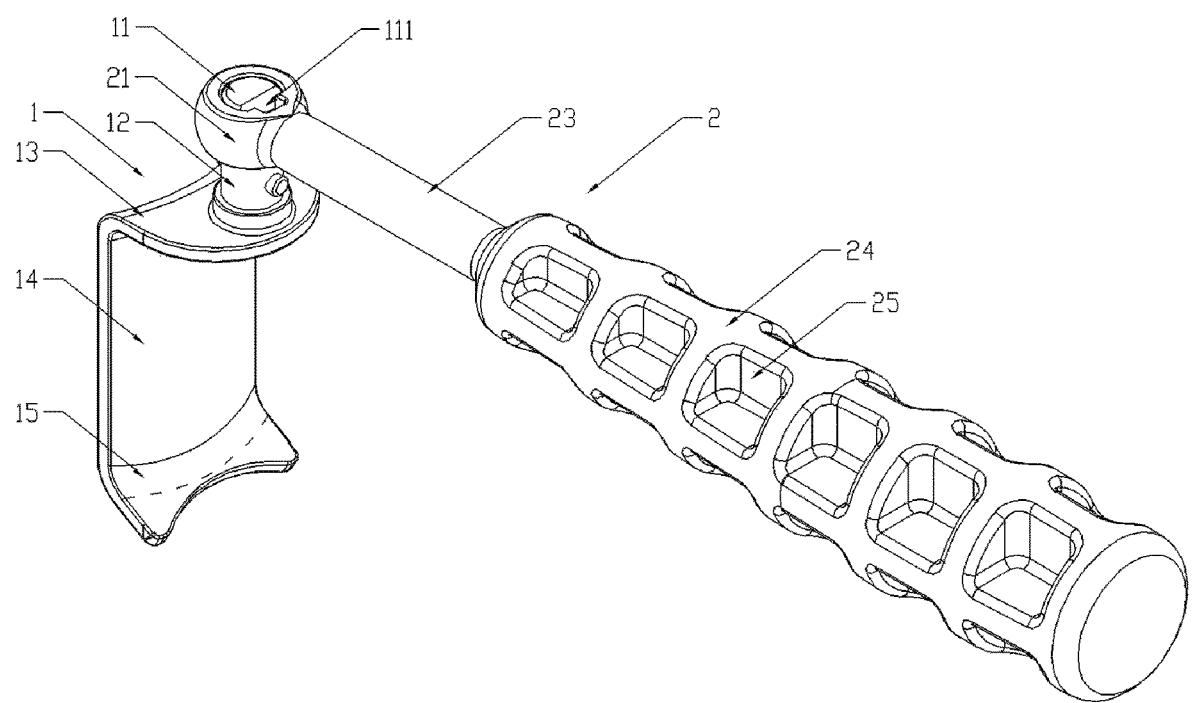
FIG. 3 is a structure diagram of the unidirectional expanding device in the invention.
Figure 4:
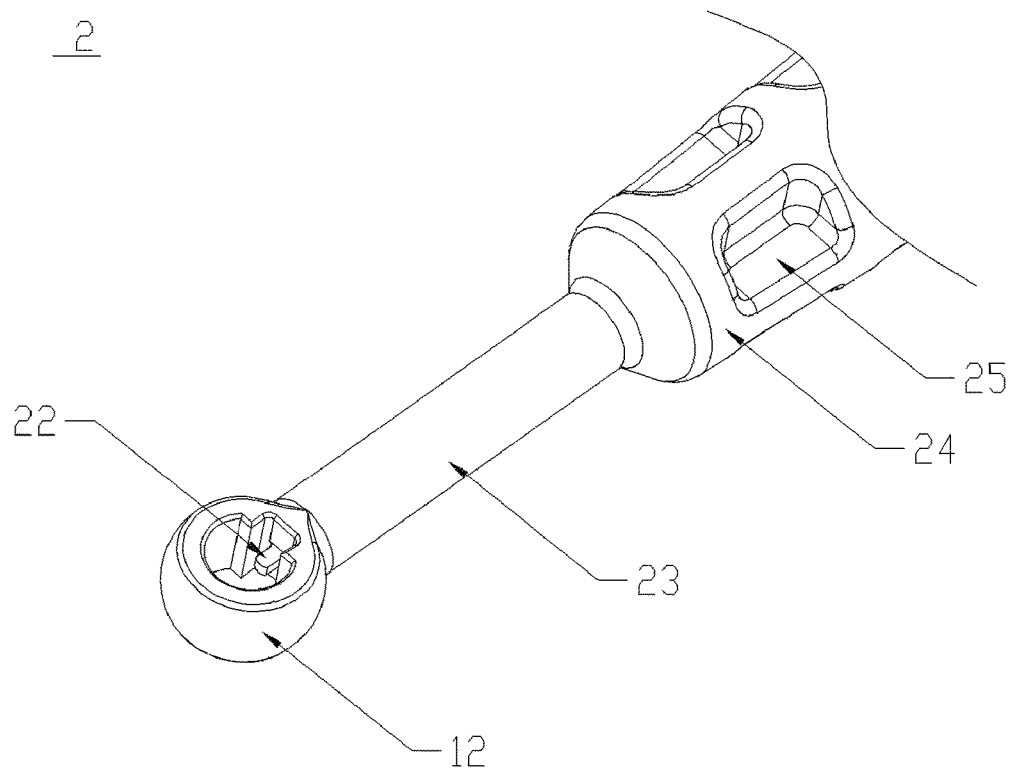
FIG. 4 is an enlarged structure diagram of the snap ring of the stretching grip in FIG. 5 in the invention.

As shown in FIG. 3 to FIG. 4, the invention puts forward a unidirectional expanding device, comprising an expanding blade 1 and a stretching grip 2 buckled to the expanding blade 1, wherein, the stretching grip 2 comprises a snap ring 21, a connecting rod 23 and a gripping arm 24 which are axially connected in a proper sequence, the stretching grip 2 is installed to the first snap-fit portion 11 through the snap ring 21, the inside diameter of the snap ring 21 is matched with the outside diameter of the first snap-fit portion 11, a butt block 22 is arranged on the inner side wall of the snap ring 21, and the butt block 22 abuts on the flat section 111. The diameter of the gripping arm 24 connected with the connecting rod 23 at one end is smaller than that at the other end, and a plurality of groove holes 25 are arranged on the gripping arm 24. When the stretching grip 2 is installed to the first snap-fit portion 11 through the snap ring 21, the oblique section 112 directly faces the butt block 22 to facilitate the butt block 22 to be just pressed against the flat section 111, and the bottom side surface of the snap ring 21 is pressed onto the convex ring 121. Wherein, the butt block 22 is arranged at the bottom side of the snap ring 21 to facilitate the butt block 22 to be the first to come into contact with the first snap-fit portion 11 during clamping, and the butt block 22 is finally pressed against the bottom side edge of the first snap-fit portion 11 to avoid easy disengagement of the snap ring 21.

Figure 5:
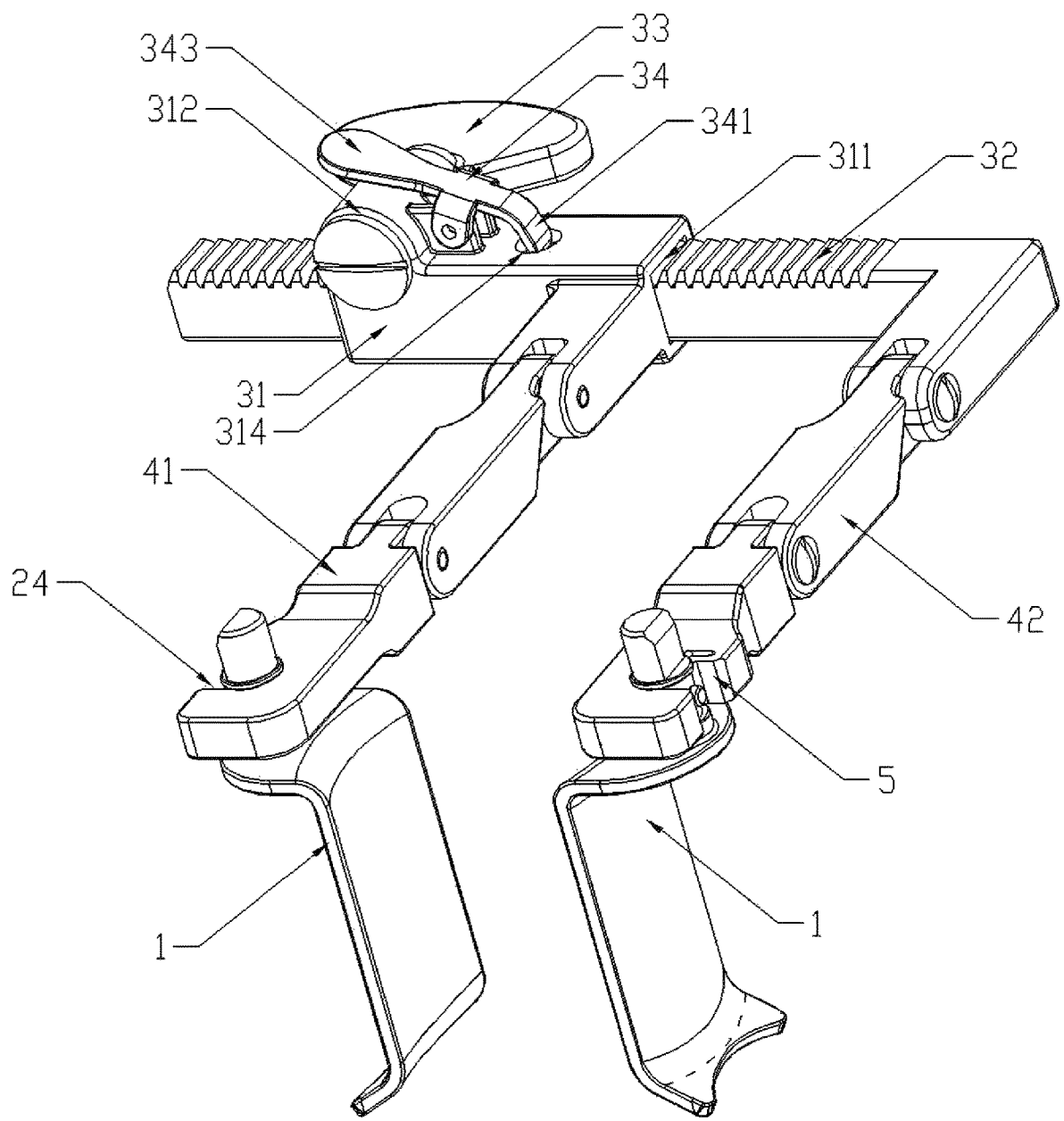
FIG. 5 is a structure diagram of the bidirectional expanding device in the invention.
Figure 6:
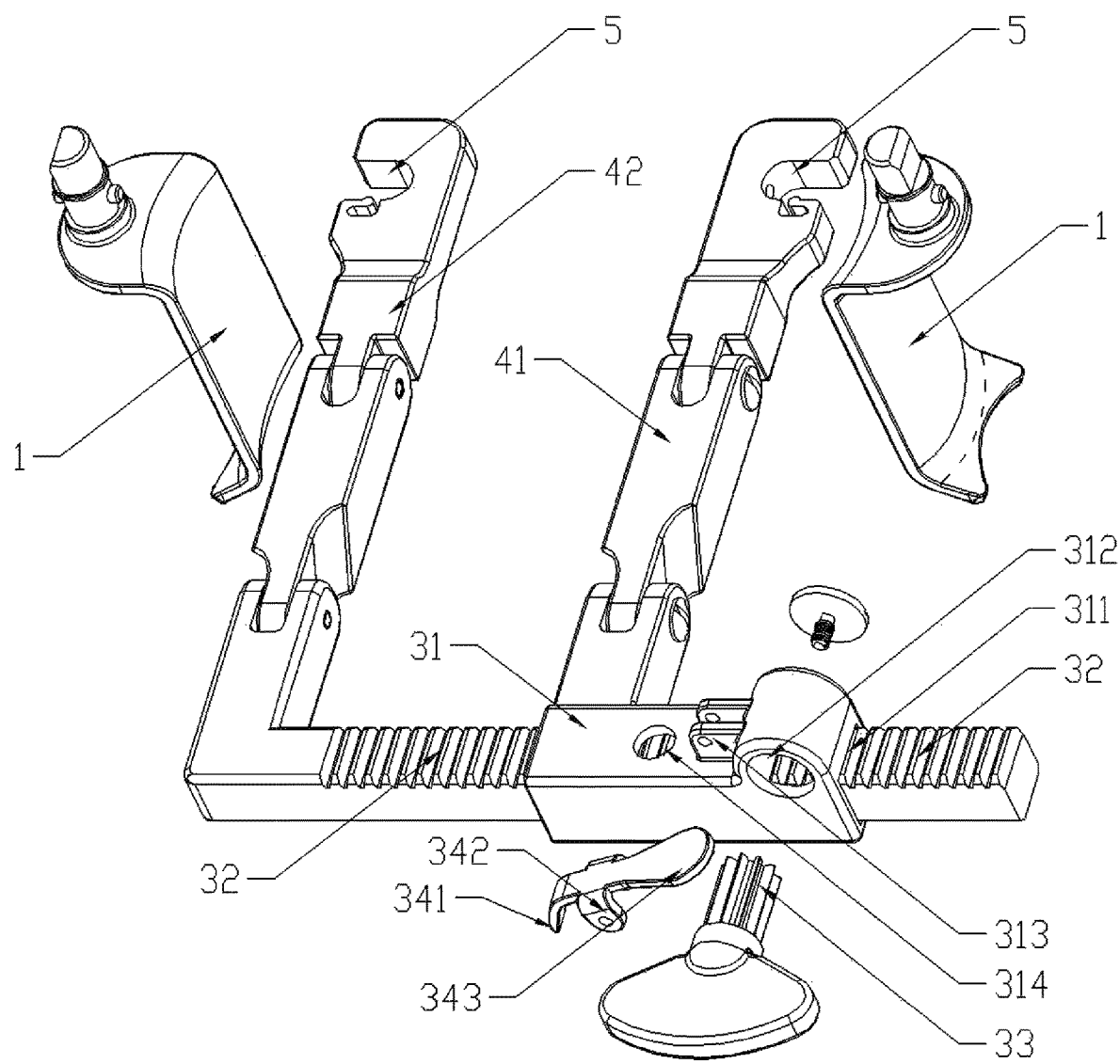
FIG. 6 is an exploded structure diagram of FIG. 5 in the invention.
Figure 7:
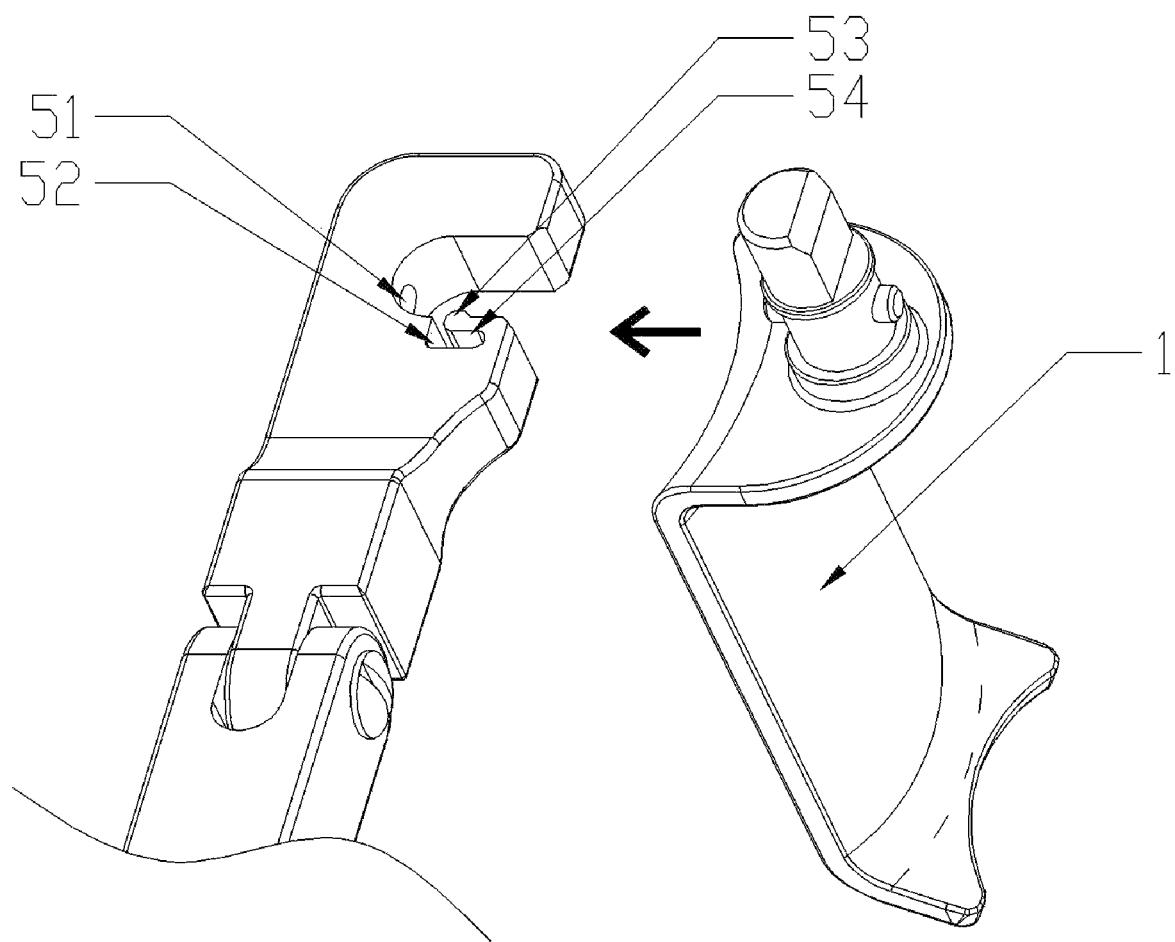
FIG. 7 is an enlarged structure diagram of the clamping groove in FIG. 6 in the invention.

As shown in FIG. 5 to FIG. 7, the invention puts forward a bidirectional expanding device, comprising a movable device, a fixed expanding arm 41, a movable expanding arm 42 and two expanding blades 1.

Specifically, as shown in FIG. 5 to FIG. 6, the movable device comprises a fixation base 31, a movable rack 32 and a tooth rotating knob 33, wherein, a buckle hole 314 to the inside of the cavity 311 is arranged on the surface of the fixation base 31, the fixation base 31 has a through cavity 311, the movable rack 32 is arranged in the cavity 311, the tooth rotating knob 33 is rotatably fixed to the fixation base 31, and the tooth rotating knob 33 is engaged with the toothed edge of the movable rack 32. Also, a through cylindrical rotation position cavity 312 is arranged on the fixation base 31, the rotation position cavity 312 is adjacent to and communicated with the cavity 311, the axis direction of the rotation position cavity 312 is perpendicular to the axis direction of the cavity 311, and a tooth rotating knob 33 is arranged in the rotation position cavity 312 to facilitate engagement of the tooth rotating knob 33 with the toothed edge of the movable rack 32.

In addition, as shown in FIG. 5 to FIG. 7, the fixed expanding arm 41 has an open groove at one end, and is connected with the fixation base 31 at the other end; the movable expanding arm 42 has the other clamping groove 5 at one end, and is connected with the movable rack 32 at the other end; the fixed expanding arm 41 and the movable expanding arm 42 are arranged in parallel, the positions of the clamping grooves 5 arranged respectively on the fixed expanding arm 41 and the movable expanding arm 42 correspond to each other, the hook edges 15 of the two expanding blades 1 are in opposite bending directions, and the clamping groove 5 clamps the second snap-fit portion 12 of the expanding blade 1; the clamping grooves 5 arranged respectively on the fixed expanding arm 41 and the movable expanding arm 42 are in opposite open end directions. Further, both the fixed expanding arm 41 and the movable expanding arm 42 are multi-segment connecting arms which can be extended by segments according to the actual demands, and the multi-segment connecting arms can be folded and rotated through connection ports to facilitate folding and storage.

To sum up, as shown in FIG. 5 to FIG. 6, the tooth rotating knob 33 rotates, the movable rack 32 moves forward and backward in the cavity 311 under the thrust force of the engaged toothed edges to adjust the horizontal distance between the fixed expanding arm 41 and the movable expanding arm 42 so that the two expanding blades 1 respectively fastened to the fixed expanding arm 41 and the movable expanding arm 42 are close to or far away from each other.

Specifically, as shown in FIG. 7, the clamping grooves 5 are U-shaped, with arc-like groove bottoms and flush edges; a locating hole 51 snap-fitted in with the locating block 123 is arranged in the center position of the groove bottom; a concave movable cavity 52 is arranged on the wall surface of the groove edge, a limiting clamping part 53 is arranged in the movable cavity 52, the limiting clamping part 53 is in the shape of a plate, the plate surface is flush with the wall surface of the groove edge, the limiting clamping part 53 is arranged on the side wall of the opening of the movable cavity 52 at one end and has a convex butt edge 54 at the other end, and the butt edge 54 oscillates inside and outside the movable cavity 52 under the action of external forces.

Further, as shown in FIG. 5 to FIG. 6, the movable device also comprises a buckle 34, a bent buckling portion 341 is arranged at one end of the buckle 34, a pressing portion 343 is arranged at the other end of the buckle 34, first convex connecting portions 342 are arranged in the middle of the buckle 34, second convex connecting portions 313 are arranged on the fixation base 31, and the first connecting portions 342 are rotatably connected with the second connecting portions 313; when the buckling portion 341 is pressed down to the bottom end, the buckling portion 341 is clamped between adjacent toothed edges of the movable rack 32, and the movable rack 32 stops moving in the cavity 311; when the pressing portion 343 is pressed, the buckling portion 341 moves upward due to the lever principle, the buckling portion 341 clamped between the adjacent toothed edges of the movable rack 32 moves out, and the movable rack 32 moves in the cavity 311 under the adjustment of the tooth rotating knob 33. The buckling portion 341 of the buckle 34 faces the buckle hole 314 in the surface of the fixation base 31, and the toothed edge of the movable rack 32 is exposed outside the fixation base 31 by the buckle hole 314 to facilitate buckling of the buckling portion 341 of the buckle 34.

The specific usage in surgery is as follows: Generate a small incision after the skin is cut open, pull the incision open with the unidirectional expanding device, after the incision is pulled open to an appropriate degree, replace it with the bidirectional expanding device, and continue to expand the incision area steadily.

To sum up, in this embodiment, two fastening structures, i.e. the first snap-fit portion and the second snap-fit portion, arranged for the expanding blade can be snap-fitted in with different devices using different installation methods. In addition, both the unidirectional expanding device and the bidirectional expanding device use the same kind of expanding blades, which reduces the number of instruments used in operations and lowers the cost, and both of them are simply fastened with simple structures, which is convenient for disassembly, assembly and replacement.

The description above is the preferred embodiment of the invention only, and has no limit to the invention. The changes in any form, such as equivalent replacements or modifications, made to the technical solution and contents disclosed in the invention by those skilled in the art without departing from the scope of the technical solution of the invention belong to the contents without departing from the technical solution of the invention, and are still within the scope of protection of the invention.

The invention claimed is:

1. An expanding blade, comprising a first snap-fit portion, a second snap-fit portion, a fixation portion, a partition panel and hook edges, wherein:
    the first snap-fit portion is columnar, and has an axial flat section on one side;
    the second snap-fit portion is columnar, is connected with the first snap-fit portion at one end and is fixed to the fixation portion at the other end, and a convex locating block is arranged on a side wall of the second snap-fit portion;
    the partition panel is connected with the fixation portion at one end, the hook edges which are inclined outwards is arranged at the other end, and both the fixation portion and the hook edges are arranged on the same side of the partition panel; and
    wherein an oblique section which is inclined to a flat section is arranged for a top side surface of the first snap-fit portion.

2. The expanding blade according to claim 1, wherein a convex ring is arranged between the first snap-fit portion and the second snap-fit portion, and diameters of both the first snap-fit portion and the second snap-fit portion are less than a diameter of the convex ring; a boss is arranged where the second snap-fit portion and the fixation portion are connected, and a diameter of the boss is greater than that of the second snap-fit portion.

3. A unidirectional expanding device using the expanding blade as described in claim 2, wherein the expanding blade is buckled with a stretching grip comprising a snap ring, a connecting rod and a gripping arm which are axially connected in a sequence, wherein the stretching grip is installed to the first snap-fit portion through the snap ring, wherein an inside diameter of the snap ring is matched with an outside diameter of the first snap-fit portion, wherein a butt block is arranged on the inner side wall of the snap ring, and wherein the butt block abuts on the flat section.

4. A bidirectional expanding device using the expanding blade as described in claim 2, comprising a movable device, a fixed expanding arm, a movable expanding arm and two expanding blades, wherein:
    the movable device comprises a fixation base, a movable rack and a tooth rotating knob, wherein, the fixation base has a through cavity, the movable rack is arranged in the cavity, the tooth rotating knob is rotatably fixed to the fixation base, and the tooth rotating knob is engaged with a toothed edge of the movable rack;
    the fixed expanding arm has a first clamping groove at one end, and is connected with the fixation base at the other end;
    the movable expanding arm has a second clamping groove at one end, and is connected with the movable rack at the other end;
    the fixed expanding arm and the movable expanding arm are arranged in parallel, the positions of the clamping grooves arranged respectively on the fixed expanding arm and the movable expanding arm correspond to each other, the hook edges of the two expanding blades are in opposite bending directions, and the second clamping groove clamps the second snap-fit portion of the expanding blade;
    the tooth rotating knob rotates, and the movable rack moves forward and backward in the cavity under a thrust force of the engaged toothed edges to adjust the horizontal distance between the fixed expanding arm and the movable expanding arm so that the two expanding blades can be respectively fastened to the fixed expanding arm and the movable expanding arm are close to or far away from each other.

5. A unidirectional expanding device using the expanding blade as described in claim 1, wherein the expanding blade is buckled with a stretching grip comprising a snap ring, a connecting rod and a gripping arm which are axially connected in a sequence, wherein the stretching grip is installed to the first snap-fit portion through the snap ring, wherein an inside diameter of the snap ring is matched with an outside diameter of the first snap-fit portion, wherein a butt block is arranged on the inner side wall of the snap ring, and wherein the butt block abuts on the flat section.

6. A bidirectional expanding device using the expanding blade as described in claim 1, comprising a movable device, a fixed expanding arm, a movable expanding arm and two expanding blades, wherein:
    the movable device comprises a fixation base, a movable rack and a tooth rotating knob, wherein, the fixation base has a through cavity, the movable rack is arranged in the cavity, the tooth rotating knob is rotatably fixed to the fixation base, and the tooth rotating knob is engaged with a toothed edge of the movable rack;
    the fixed expanding arm has a first clamping groove at one end, and is connected with the fixation base at the other end;
    the movable expanding arm has a second clamping groove at one end, and is connected with the movable rack at the other end;
    the fixed expanding arm and the movable expanding arm are arranged in parallel, the positions of the clamping grooves arranged respectively on the fixed expanding arm and the movable expanding arm correspond to each other, the hook edges of the two expanding blades are in opposite bending directions, and the second clamping groove clamps the second snap-fit portion of the expanding blade;

the tooth rotating knob rotates, and the movable rack moves forward and backward in the cavity under a thrust force of the engaged toothed edges to adjust the horizontal distance between the fixed expanding arm and the movable expanding arm so that the two expanding blades can be respectively fastened to the fixed expanding arm and the movable expanding arm are close to or far away from each other.

7. A unidirectional expanding device using an expanding blade, comprising a first snap-fit portion, a second snap-fit portion, a fixation portion, a partition panel and hook edges, wherein:

the first snap-fit portion is columnar, and has an axial flat section on one side;

the second snap-fit portion is columnar, is connected with the first snap-fit portion at one end and is fixed to the fixation portion at the other end, and a convex locating block is arranged on a side wall of the second snap-fit portion;

the partition panel is connected with the fixation portion at one end, the hook edges which are inclined outwards is arranged at the other end, and both the fixation portion and the hook edges are arranged on the same side of the partition panel; and wherein the expanding blade is buckled with a stretching grip comprising a snap ring, a connecting rod and a gripping arm which are axially connected in a sequence, wherein the stretching grip is installed to the first snap-fit portion through the snap ring, wherein an inside diameter of the snap ring is matched with an outside diameter of the first snap-fit portion, wherein a butt block is arranged on the inner side wall of the snap ring, and wherein the butt block abuts on the flat section.

8. A bidirectional expanding device using an expanding blade, comprising a first snap-fit portion, a second snap-fit portion, a fixation portion, a partition panel and hook edges, wherein:

the first snap-fit portion is columnar, and has an axial flat section on one side;

the second snap-fit portion is columnar, is connected with the first snap-fit portion at one end and is fixed to the fixation portion at the other end, and a convex locating block is arranged on a side wall of the second snap-fit portion;

the partition panel is connected with the fixation portion at one end, the hook edges which are inclined outwards is arranged at the other end, and both the fixation portion and the hook edges are arranged on the same side of the partition panel; and wherein the bidirectional expanding device comprises a movable device, a fixed expanding arm, a movable expanding arm and two expanding blades, wherein:

the movable device comprises a fixation base, a movable rack and a tooth rotating knob, wherein, the fixation base has a through cavity, the movable rack is arranged in the cavity, the tooth rotating knob is rotatably fixed to the fixation base, and the tooth rotating knob is engaged with a toothed edge of the movable rack;

the fixed expanding arm has a first clamping groove at one end, and is connected with the fixation base at the other end;

the movable expanding arm has a second clamping groove at one end, and is connected with the movable rack at the other end;

the fixed expanding arm and the movable expanding arm are arranged in parallel, the positions of the clamping grooves arranged respectively on the fixed expanding arm and the movable expanding arm correspond to each other, the hook edges of the two expanding blades are in opposite bending directions, and the second clamping groove clamps the second snap-fit portion of the expanding blade;

the tooth rotating knob rotates, and the movable rack moves forward and backward in the cavity under a thrust force of the engaged toothed edges to adjust the horizontal distance between the fixed expanding arm and the movable expanding arm so that the two expanding blades can be respectively fastened to the fixed expanding arm and the movable expanding arm are close to or far away from each other.

9. The bidirectional expanding device according to claim 8, wherein the clamping grooves arranged respectively on the fixed expanding arm and the movable expanding arm are in opposite open end directions.

10. The bidirectional expanding device according to claim 9, wherein the clamping grooves are U-shaped and have arc-like groove bottoms and flush edges;

wherein a locating hole snap-fitted in with the locating block is arranged in the center position of the groove bottom;

wherein a concave movable cavity is arranged on a wall surface of the groove edge, a limiting clamping part is arranged in the movable cavity, the limiting clamping part is in the shape of a plate, the plate surface is flush with a wall surface of the groove edge, the limiting clamping part is arranged on a side wall of the opening of the movable cavity at one end and has a convex butt edge at the other end, and the butt edge oscillates inside and outside the movable cavity under the action of external forces.

11. The bidirectional expanding device according to claim 8, wherein the movable device also comprises a buckle, wherein, the buckle has a bent buckling portion at one end and a pressing portion at the other end, first convex connecting portions are arranged in the middle of the buckle, second convex connecting portions are arranged on the fixation base, and the first connecting portions are rotatably connected with the second connecting portions; when the buckling portion is pressed down to the bottom end, the buckling portion is clamped between adjacent toothed edges of the movable rack, and the movable rack stops moving in the cavity; when the pressing portion is pressed, the buckling portion moves upward due to the lever principle, the buckling portion clamped between the adjacent toothed edges of the movable rack moves out, and the movable rack moves in the cavity under the adjustment of the tooth rotating knob.

* * * * *